United States Patent
Ogawa

(10) Patent No.: US 9,782,058 B2
(45) Date of Patent: Oct. 10, 2017

(54) ENDOSCOPE

(71) Applicant: OLYMPUS CORPORATION, Tokyo (JP)

(72) Inventor: Tomoaki Ogawa, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/149,251

(22) Filed: May 9, 2016

(65) Prior Publication Data

US 2016/0249792 A1 Sep. 1, 2016

Related U.S. Application Data

(63) Continuation of application No. PCT/JP2015/061631, filed on Apr. 15, 2015.

(30) Foreign Application Priority Data

Jul. 17, 2014 (JP) ................. 2014-147067

(51) Int. Cl.
*A61B 1/012* (2006.01)
*A61B 1/00* (2006.01)
(Continued)

(52) U.S. Cl.
CPC ............... *A61B 1/012* (2013.01); *A61B 1/00* (2013.01); *A61B 1/00119* (2013.01);
(Continued)

(58) Field of Classification Search
CPC ............. Y10S 600/92; A61B 1/00064; A61B 1/00066; A61B 1/00068; A61B 1/00082; A61B 1/0011; A61B 1/00112; A61B 1/00114; A61B 1/00119; A61B 1/00121; A61B 1/00128; A61B 1/00137; A61B 1/012; A61B 1/015; A61B 1/018;
(Continued)

(56) References Cited

U.S. PATENT DOCUMENTS 4,552,129 A * 11/1985 Utsugi ............... A61B 1/00137
600/131
4,705,023 A * 11/1987 Arai ....................... A61B 1/018
600/104
(Continued)

FOREIGN PATENT DOCUMENTS

EP  2 659 828 A1  11/2013
JP  S62-102732 A  5/1987
JP  2010-207424 A  9/2010

OTHER PUBLICATIONS

International Search Report dated Jun. 30, 2015 issued in PCT/JP2015/061631.
(Continued)

*Primary Examiner* — Ryan Henderson
(74) *Attorney, Agent, or Firm* — Scully, Scott, Murphy & Presser, PC

(57) ABSTRACT

An endoscope includes an insertion portion; an operation portion; a balloon water injection channel; a first opening portion; a balloon pipe sleeve provided with a first end portion and a second end portion; a branch channel connection unit; a rotation restriction portion; and a connecting tube on which the branch channel connection unit is assembled.

4 Claims, 9 Drawing Sheets

(51) Int. Cl.
*A61B 8/12* (2006.01)
*A61M 25/00* (2006.01)

(52) U.S. Cl.
CPC ............ *A61B 1/00128* (2013.01); *A61B 8/12* (2013.01); *A61M 25/0028* (2013.01)

(58) Field of Classification Search
CPC ........... A61B 8/12; A61B 8/44; A61B 8/4444; A61B 8/445; A61B 8/4455; A61B 8/4461; A61B 8/4466
USPC ................ 600/104, 106, 107, 131, 153, 154
See application file for complete search history.

(56) References Cited

U.S. PATENT DOCUMENTS

| | | | | |
|---|---|---|---|---|
| 4,750,477 | A * | 6/1988 | Wardle | A61B 1/0051 600/133 |
| 4,765,312 | A * | 8/1988 | Sasa | A61B 1/00068 600/153 |
| 4,791,912 | A | 12/1988 | Tashiro | |
| 4,972,828 | A * | 11/1990 | Ito | A61B 1/00137 600/153 |
| 5,667,477 | A * | 9/1997 | Segawa | A61B 1/018 600/101 |
| 5,735,793 | A * | 4/1998 | Takahashi | A61B 1/00059 600/104 |
| 5,810,718 | A * | 9/1998 | Akiba | A61B 1/00128 600/153 |
| 2004/0193183 | A1 * | 9/2004 | Akiba | A61B 17/06066 606/139 |
| 2007/0088199 | A1 * | 4/2007 | Ito | A61B 1/00137 600/156 |
| 2007/0118016 | A1 * | 5/2007 | Frimberger | A61B 1/018 600/154 |
| 2012/0172667 | A1 * | 7/2012 | Takeuchi | A61B 1/0052 600/140 |
| 2013/0274550 | A1 * | 10/2013 | Takeuchi | A61B 1/018 600/104 |

OTHER PUBLICATIONS

Japanese Office Action dated Nov. 17, 2015 issued in JP 2015-544269.
Extended Supplementary European Search Report dated Jun. 6, 2017 in European Patent Application No. 15 82 2187.9.

* cited by examiner

ENDOSCOPE

CROSS REFERENCE TO RELATED APPLICATION

This application is a continuation application of PCT/JP2015/061631 filed on Apr. 15, 2015 and claims benefit of Japanese Application No. 2014-147067 filed in Japan on Jul. 17, 2014, the entire contents of which are incorporated herein by this reference.

BACKGROUND OF THE INVENTION

1. Field of the Invention

The present invention relates to an endoscope equipped with a branch channel communicated with a first opening portion of a main channel in an operation portion.

2. Description of the Related Art

A configuration in which a tubular main channel is provided inside an insertion portion or an operation portion of an endoscope is well-known, where the insertion portion is inserted into a subject and the operation portion is connected to a proximal end of the insertion portion in an insertion axis direction.

Note that examples of the main channel include a treatment instrument insertion channel through which a treatment instrument is supplied into the subject and a balloon water injection channel through which an ultrasound transmission medium is supplied to a balloon provided in an insertion portion of an ultrasound endoscope.

The main channel includes a first opening portion which opens in an operation portion, and the first opening portion is communicated with a first end portion of a tubular branch channel whose second end portion opens outside the operation portion.

The branch channel is intended to supply a treatment instrument, ultrasound transmission medium, or the like to a main channel from the operation portion and is connected to the main channel in the operation portion such that the first end portion will be communicated with the first opening portion of the main channel. Note that examples of the branch channel include a treatment instrument insertion pipe sleeve and a balloon pipe sleeve connected with a syringe used to inject the ultrasound transmission medium.

Also, Japanese Patent Application Laid-Open Publication No. 2010-207424 discloses a configuration in which D-cuts are made in an inner circumferential face of a branch channel mounting hole provided in an operation portion and an outer circumferential face of a branch channel fitted in the branch channel mounting hole, and with the D-cut in the outer circumferential face of the branch channel and the D-cut in the inner circumferential face of the branch channel mounting hole abutting against each other, the branch channel is screw-fastened, preventing rotation of the branch channel after the fastening.

Now, if a tilting force is applied to the branch channel during operation of the endoscope, a tilting force is applied to a fixing section of the branch channel as well.

Note that cases in which the tilting force of the branch channel is applied include a case in which when the insertion portion is twisted with respect to the operation portion or when part of a grip of the operation portion provided with the branch channel is configured to be rotatable together with the branch channel, the part of the grip is rotated.

SUMMARY OF THE INVENTION

An endoscope according to one aspect of the invention includes: an insertion portion inserted into a subject; an operation portion connected to a proximal end side of the insertion portion; a main channel configured to be tubular and placed in the insertion portion; a first opening portion formed at a proximal end of the main channel on a side of the operation portion; a branch channel provided with a first end portion and a second end portion, where the second end portion opens outside the operation portion; a branch channel connection unit connected so as to be communicated with the first opening portion of the main channel and the first end portion of the branch channel; a rotation restriction portion provided on the branch channel connection unit; and a connecting tube which is fitted in the rotation restriction portion and fixed to the operation portion, and on which the branch channel connection unit is assembled.

DETAILED DESCRIPTION OF THE PREFERRED EMBODIMENTS

Hereinafter, an embodiment of the present invention will be described with reference to the drawings. In the following description, note that the drawings in the embodiment are schematic, that a relationship between thickness and width of each component as well as ratios of the thickness among individual components are different from actual ones, and that dimensional relationships or ratios may not be uniform among the drawings.

Note that in the present embodiment shown below, an endoscope will be described by taking an ultrasound endoscope as an example.

Also, description will be given by citing a balloon water injection channel configured to supply an ultrasound transmission medium to a balloon provided in the insertion portion as a tubular main channel placed in an insertion portion and operation portion of the endoscope, and citing a balloon pipe sleeve connected with a syringe to inject the ultrasound transmission medium as a tubular branch channel.

Figure 1:
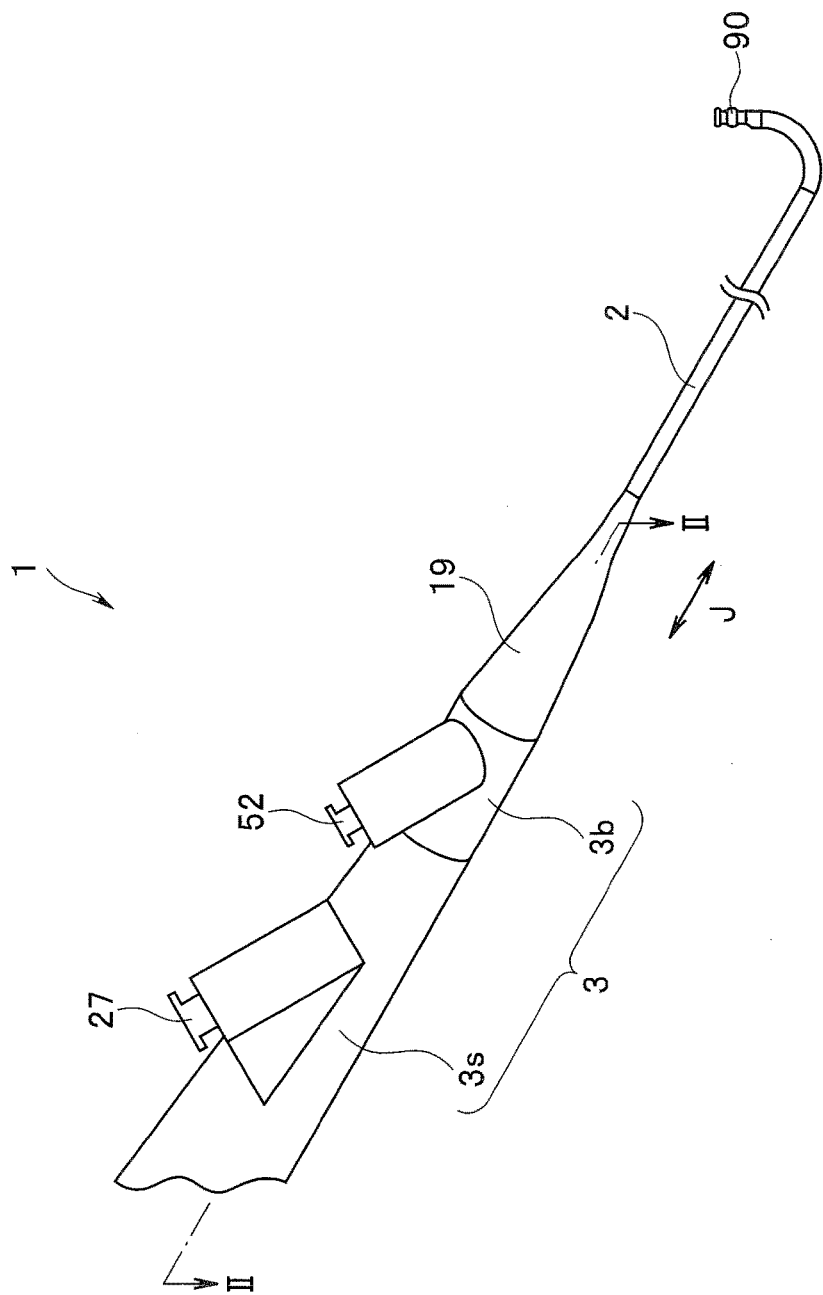
FIG. 1 is a partial perspective view schematically showing part of an insertion portion and operation portion of an endoscope according to an embodiment of the present invention.
Figure 2:
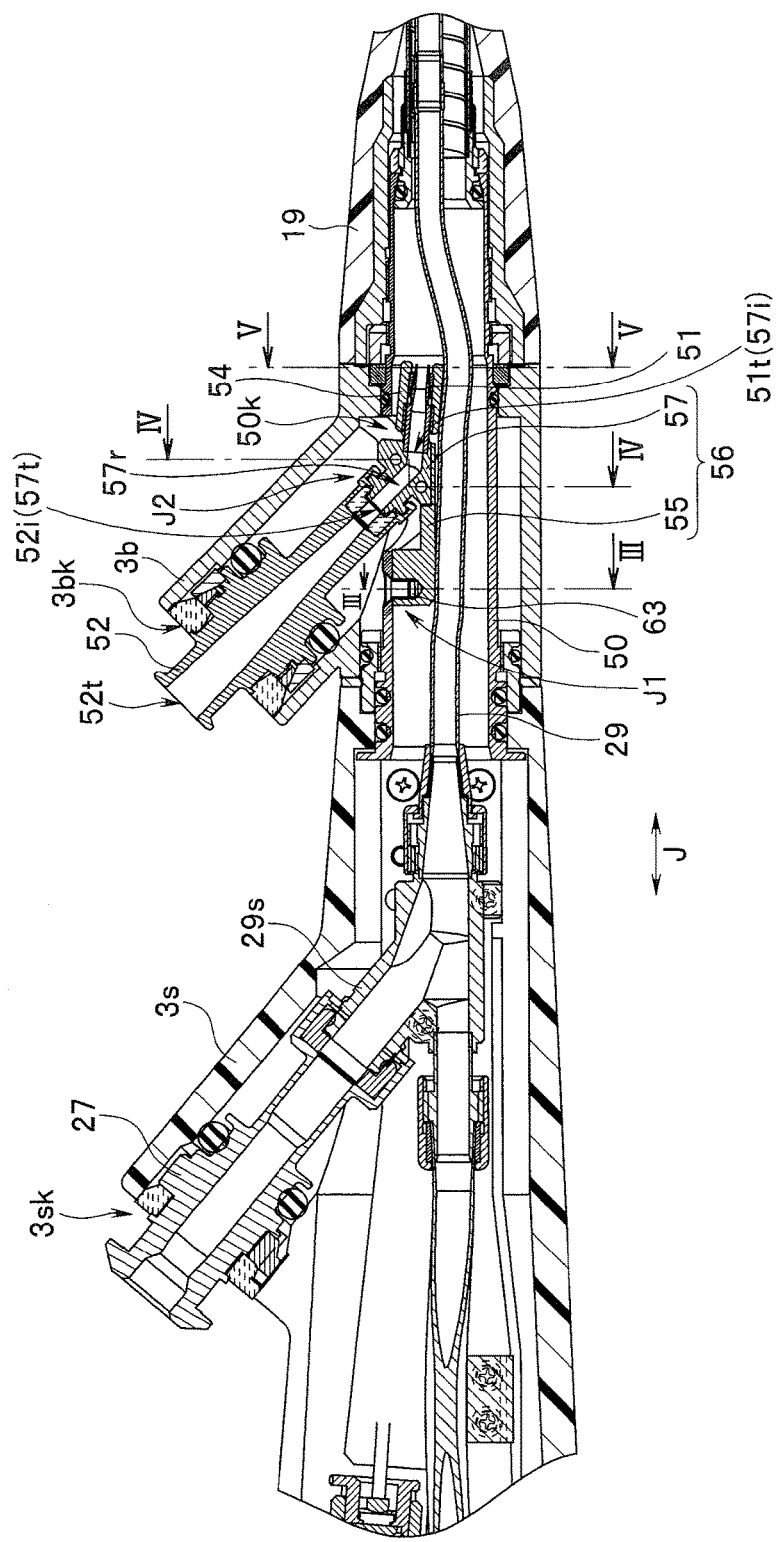
FIG. 2 is a sectional view of a bend preventer and the operation portion taken along line II-II in FIG. 1.
Figure 3:
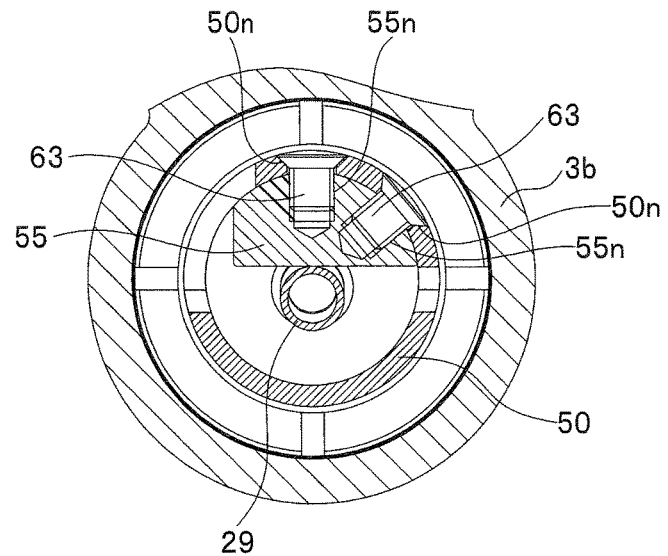
FIG. 3 is a sectional view of the operation portion taken along line in FIG. 2.
Figure 4:
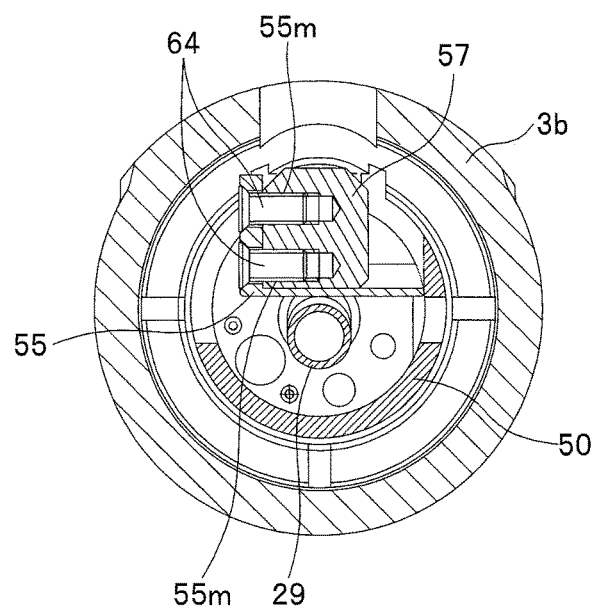
FIG. 4 is a sectional view of the operation portion taken along line IV-IV in FIG. 2.
Figure 5:
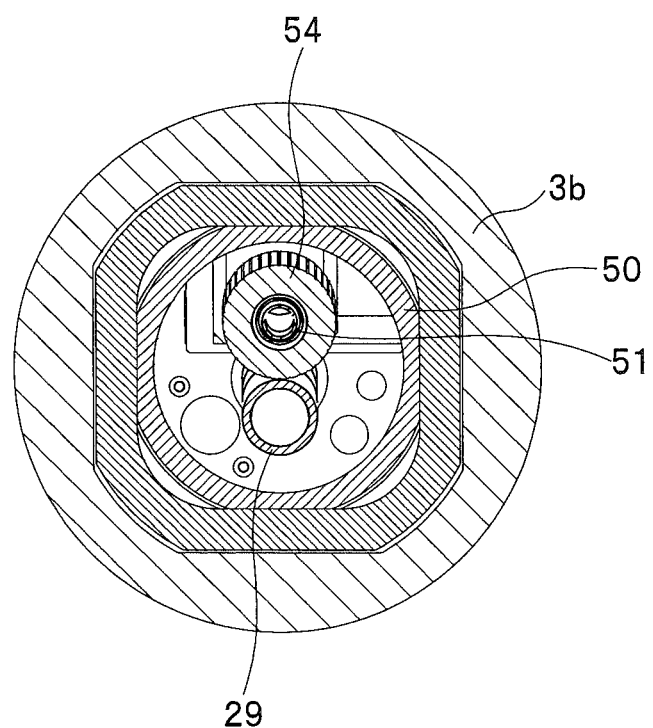
FIG. 5 is a sectional view of the operation portion taken along line V-V in FIG. 2.

FIG. 1 is a partial perspective view schematically showing part of an insertion portion and operation portion of an endoscope according to the present embodiment; FIG. 2 is a sectional view of a bend preventer and the operation portion taken along line II-II in FIG. 1; FIG. 3 is a sectional view of the operation portion taken along line in FIG. 2; FIG. 4 is a sectional view of the operation portion taken along line IV-IV in FIG. 2; and FIG. 5 is a sectional view of the operation portion taken along line V-V in FIG. 2.

Figure 6:
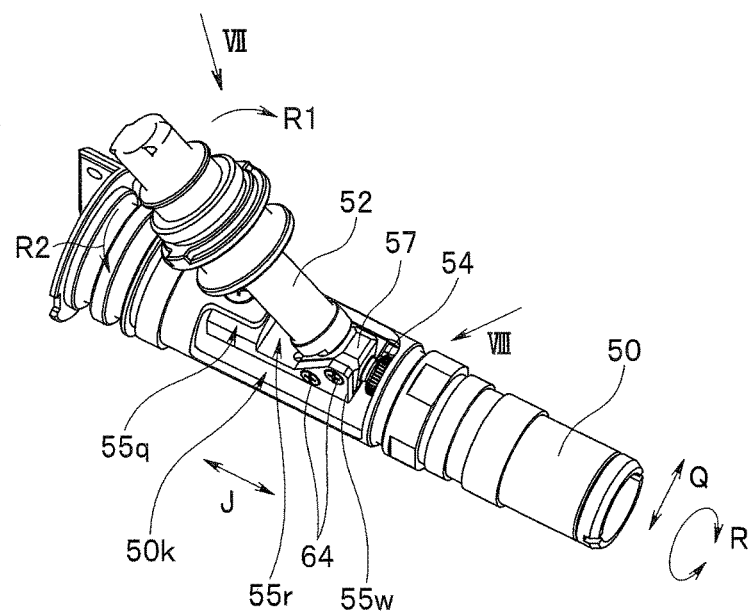
FIG. 6 is a perspective view showing a fixing structure for a balloon pipe sleeve by removing a balloon channel side grip from the operation portion of FIG. 1, where a branch channel connection unit for a balloon water injection channel is used.
Figure 7:
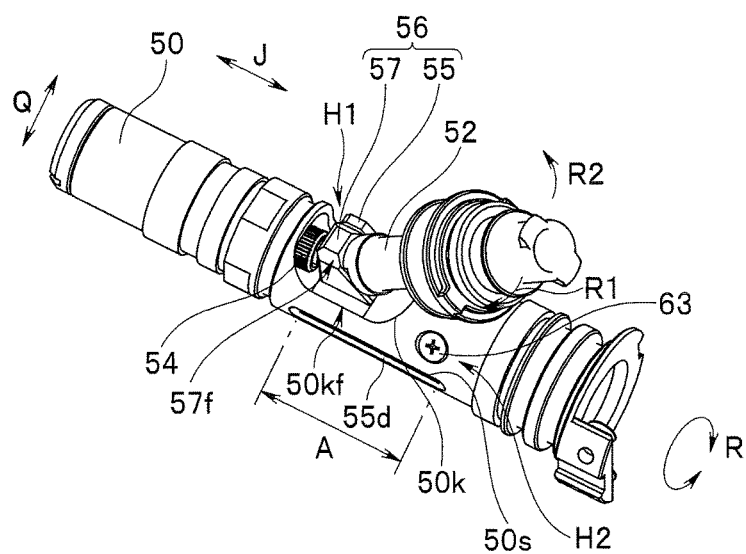
FIG. 7 is a perspective view of the fixing structure of FIG. 6 as viewed in a direction of VII in FIG. 6.
Figure 8:
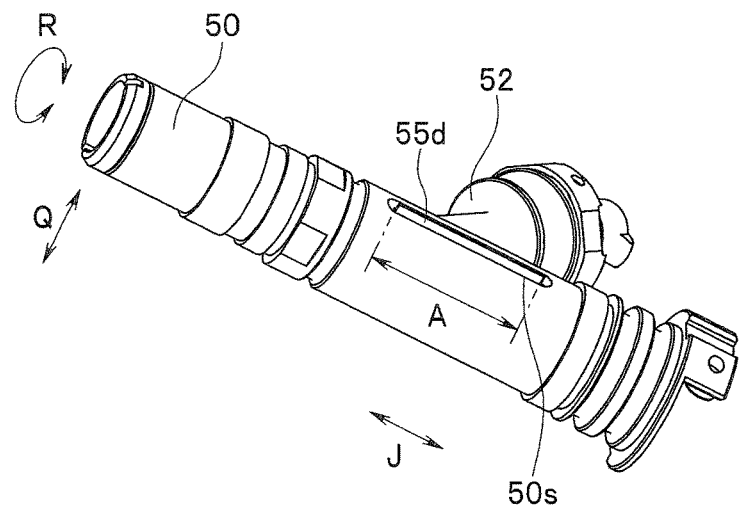
FIG. 8 is a perspective view of the fixing structure of FIG. 6 as viewed in a direction of VIII in FIG. 6.

Also, FIG. 6 is a perspective view showing a fixing structure for a balloon pipe sleeve by removing a balloon channel side grip from the operation portion of FIG. 1, where a branch channel connection unit for a balloon water injection channel is used; FIG. 7 is a perspective view of the fixing structure of FIG. 6 as viewed in a direction of VII in FIG. 6; and FIG. 8 is a perspective view of the fixing structure of FIG. 6 as viewed in a direction of VIII in FIG. 6.

Figure 9:
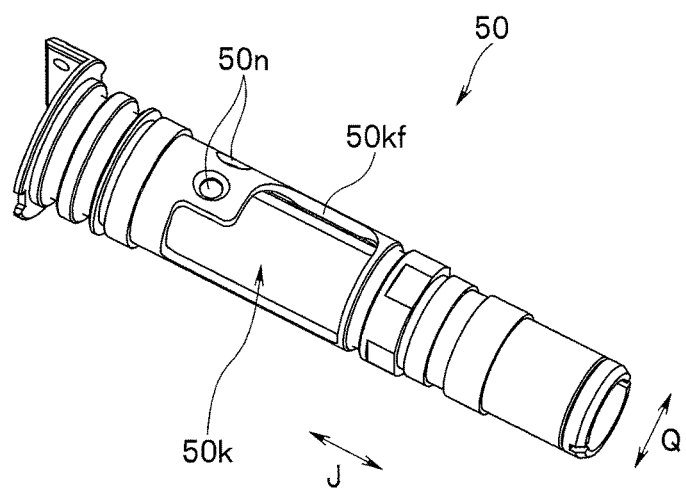
FIG. 9 is a perspective view of a connecting tube of FIG. 6.
Figure 10:
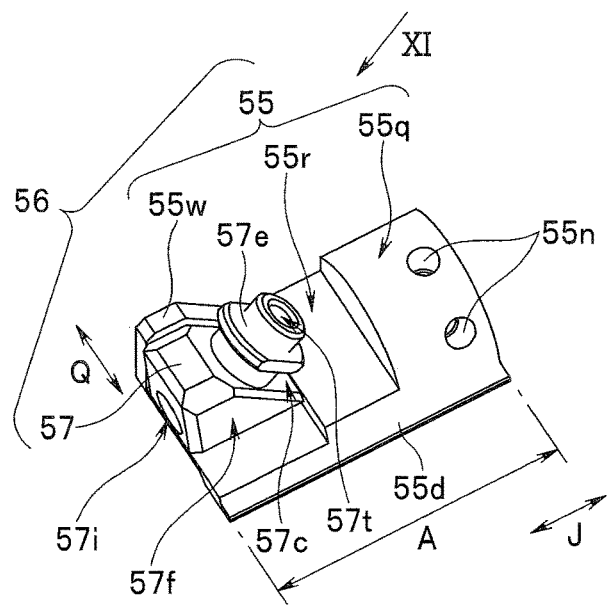
FIG. 10 is a perspective view of the branch channel connection unit of FIG. 6.
Figure 11:
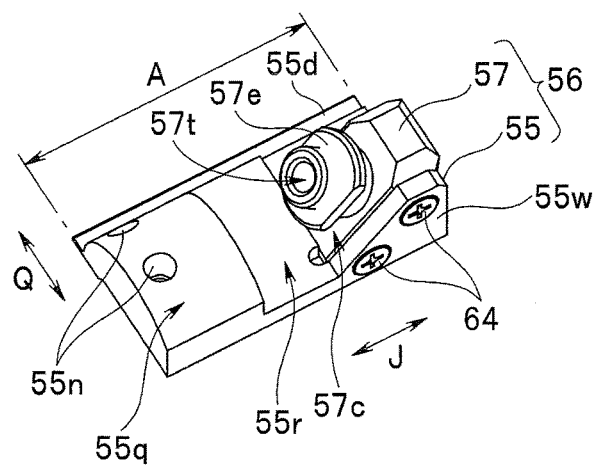
FIG. 11 is a perspective view of the branch channel connection unit of FIG. 10 as viewed in a direction of XI in FIG. 10.

Furthermore, FIG. 9 is a perspective view of a connecting tube of FIG. 6; FIG. 10 is a perspective view of the branch channel connection unit of FIG. 6; and FIG. 11 is a perspective view of the branch channel connection unit of FIG. 10 as viewed in a direction of XI in FIG. 10.

Figure 12:
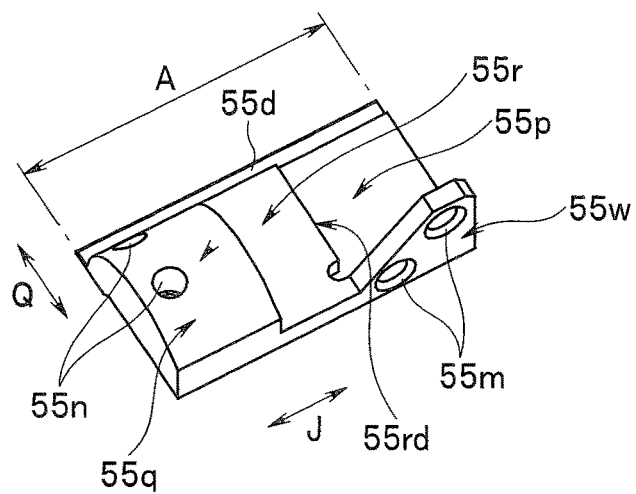
FIG. 12 is a perspective view of a pressing member in the branch channel connection unit of FIG. 10.
Figure 13:
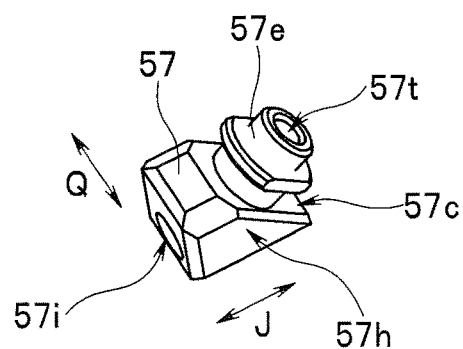
FIG. 13 is a perspective view of a block unit in the branch channel connection unit of FIG. 10.

Besides, FIG. 12 is a perspective view of a pressing member in the branch channel connection unit of FIG. 10; and FIG. 13 is a perspective view of a block unit in the branch channel connection unit of FIG. 10.

As shown in FIG. 1, an endoscope 1 includes an insertion portion 2 inserted into a subject and an operation portion 3 connected to a proximal end of the insertion portion 2 in an insertion axis direction J via a bend preventer 19.

An ultrasound transducer unit 30 described later (see FIG. 14) is provided on a distal end side of the insertion portion 2 in the insertion axis direction J.

Note that examples of the ultrasound transducer unit 30 include an electronic radial ultrasound transducer unit which has a non-illustrated ultrasound transducer in a non-illustrated housing and a non-illustrated acoustic lens on an outer surface, where the ultrasound transducer is capable of ultrasound transmission and reception in 360-degree directions and the acoustic lens is exposed circumferentially from the housing. Also, the ultrasound transducer unit 30 is not limited to an electronic radial type.

Also, on the distal end side of the insertion portion 2 in the insertion axis direction J, a balloon 90 is fitted around an outer circumference of the ultrasound transducer unit 30. A known ultrasound transmission medium has been injected in the balloon 90.

Also, on a distal end side of the operation portion 3 in the insertion axis direction J, a balloon channel side grip 3b and a treatment instrument insertion channel side grip 3s making up an exterior of the operation portion 3 are provided by being connected to a proximal end of the bend preventer 19 in the insertion axis direction J.

Note that the treatment instrument insertion channel side grip 3s is connected to a proximal end of the balloon channel side grip 3b in the insertion axis direction J.

Also, to simplify a structure of the balloon channel side grip 3b, the balloon channel side grip 3b may be rotatable relative to the treatment instrument insertion channel side grip 3s and bend preventer 19.

Also, various incorporated components are provided in the insertion portion 2 and operation portion 3, including a known signal cable, image guide, light guide, fluid supply conduit, and bending wire as well as an ultrasound transducer cable 40 (see FIG. 14) described later.

Here, as shown in FIG. 2 a treatment instrument insertion channel 29 is provided in the insertion portion 2 and operation portion 3, opening at one end in a distal end of the insertion portion 2 in the insertion axis direction J and opening at another end in an after-mentioned endoscope connector 5 of the endoscope 1.

As shown in FIG. 2, the treatment instrument insertion channel 29 is branched in the treatment instrument insertion channel side grip 3s and the branched channel 29s is connected to a treatment instrument insertion pipe sleeve 27.

The treatment instrument insertion pipe sleeve 27 is inserted in the treatment instrument insertion channel side grip 3s in a watertight manner through an opening 3sk formed in the treatment instrument insertion channel side grip 3s, being tilted at a predetermined angle with respect to the insertion axis direction J.

Also, the treatment instrument insertion pipe sleeve 27 is communicated at a first end with the treatment instrument insertion channel 29 and opens at a second end outside the operation portion 3.

Consequently, after inserting a treatment instrument into the treatment instrument insertion pipe sleeve 27 through an opening in the second end of the treatment instrument insertion pipe sleeve 27, an operator can cause the treatment instrument to pass through the treatment instrument insertion channel 29 and to protrude from the distal end of the insertion portion 2 in the insertion axis direction J.

Also, as shown in FIG. 2, a balloon water injection channel 51 is provided in the insertion portion 2 and operation portion 3.

At one end, the balloon water injection channel 51 is connected to and communicated with the balloon 90 provided in the insertion portion 2, and opens at another end as a first opening portion 51t in the balloon channel side grip 3b.

The first opening portion 51t is connected to a first end portion 52i of the balloon pipe sleeve 52 through a branch channel connection unit 56 described later.

The balloon pipe sleeve 52 is inserted in a watertight manner into the balloon channel side grip 3b through an opening 3bk formed in the balloon channel side grip 3b, by being tilted at a predetermined angle with respect to the insertion axis direction J.

The first end portion 52i of the balloon pipe sleeve 52 is communicated with the first opening portion 51t through the branch channel connection unit 56 and a second end portion 52t opens outside the operation portion 3.

Consequently, the operator can supply the ultrasound transmission medium to the balloon 90 through the balloon pipe sleeve 52 and balloon water injection channel 51 using an after-mentioned syringe 200 (see FIG. 14) connected to an opening of the second end portion 52t.

Also, as shown in FIGS. 2 to 9, a connecting tube 50 is provided in the balloon channel side grip 3b, with the balloon water injection channel 51 passed through the connecting tube 50.

The connecting tube 50 is designed to interconnect the bend preventer 19 and treatment instrument insertion channel side grip 3s along the insertion axis direction J, a proximal end of the connecting tube 50 in the insertion axis direction J is fixed to a distal end side of the treatment instrument insertion channel side grip 3s by a screw or the like. Note that the connecting tube 50 is detachably connected to the treatment instrument insertion channel side grip 3s.

Figure 14:
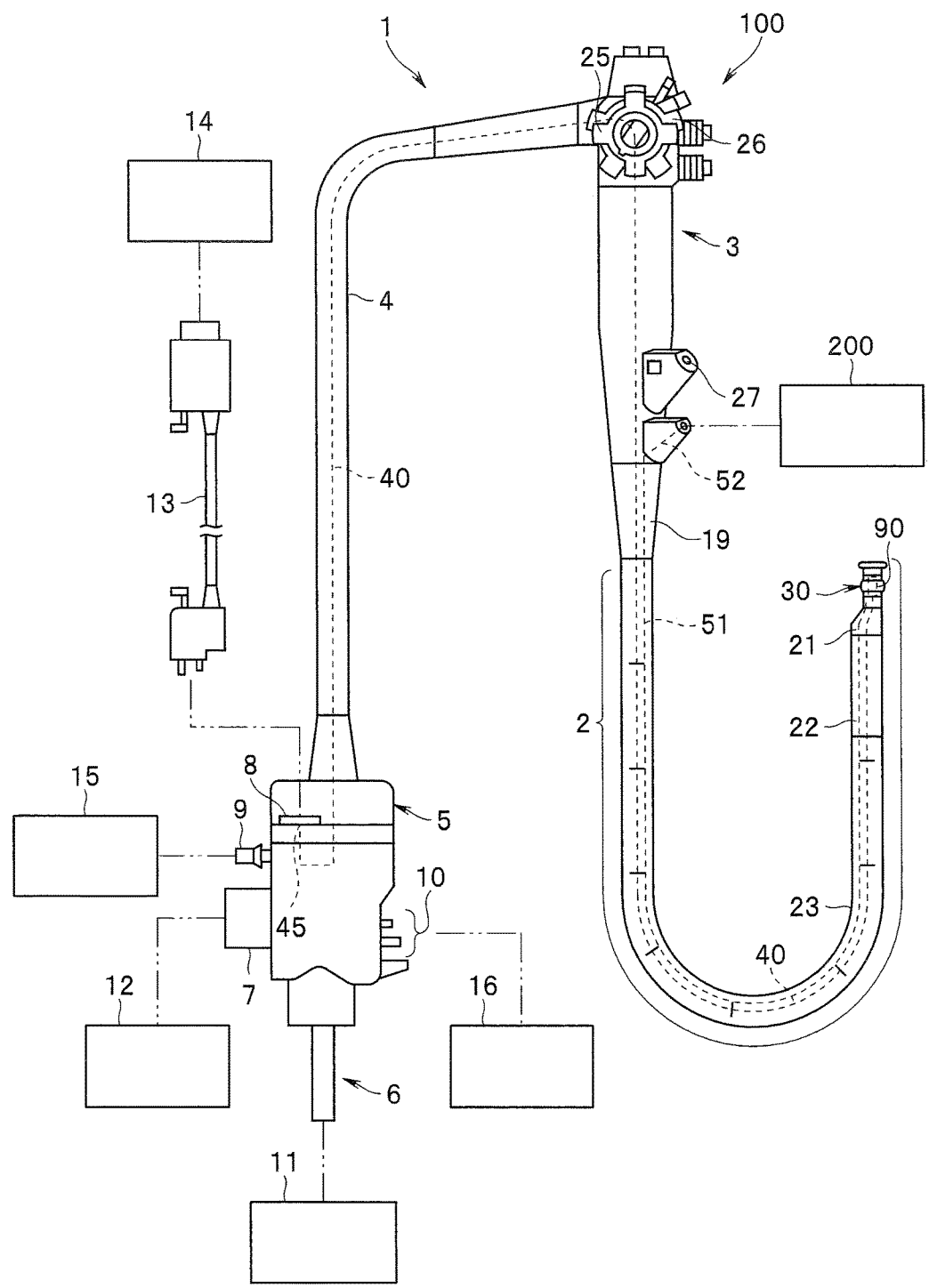
FIG. 14 is a diagram showing an ultrasound endoscope apparatus equipped with an ultrasound endoscope of FIG. 1.

Also, in addition to the balloon water injection channel 51, various incorporated components are passed through the connecting tube 50 including the above-mentioned signal cable, image guide, light guide, fluid supply conduit, bending wire, treatment instrument insertion channel 29, and ultrasound transducer cable 40 (see FIG. 14).

Also, as shown in FIGS. 2, 6, 7, and 9, a second opening portion 50k is formed at an intermediate position of the connecting tube 50 in the insertion axis direction J, where the second opening portion 50k exposes an interior of the connecting tube 50 outside and is communicated with the first opening portion 51t located inside the connecting tube 50 when the branch channel connection unit 56 is not connected to the first opening portion 51t.

As shown in FIG. 9, the second opening portion 50k has the shape of, for example, a letter L in planar shape and has an opening of a predetermined size, where the opening is used to introduce the first end portion 52i of the balloon pipe sleeve 52 and the branch channel connection unit 56 into the connecting tube 50 during assembly.

Note that the first end portion 52i of the balloon pipe sleeve 52 is passed through the second opening portion 50k, and connected to the first opening portion 51t so as to be communicated with the first opening portion 51t when the branch channel connection unit 56 is not connected to the first opening portion 51t.

Also, as shown in FIGS. 7 and 8, a notch 50s is formed in the connecting tube 50, at a position different from the second opening portion 50k, exposing the interior of the connecting tube 50 to the outside and extending a predetermined length along the insertion axis direction J.

As shown in FIGS. 2, 10, and 11, the branch channel connection unit 56 includes a pressing member 55 and a block unit 57.

As shown in FIG. 12, the pressing member 55 includes a block unit mounting portion 55p located on a distal end side in the insertion axis direction J and a block unit fixing portion 55w standing up from an end portion of the block unit mounting portion 55p in a direction Q orthogonal to the insertion axis direction J.

Also, the pressing member 55 includes a block unit positioning portion 55r and a connecting tube fixing portion 55q, where the block unit positioning portion 55r is provided with a stepped portion 55rd abutted by the block unit 57 installed consecutively with a proximal end of the block unit mounting portion 55p in the insertion axis direction while the connecting tube fixing portion 55q is shaped like an arc and installed consecutively with a proximal end of the block unit positioning portion 55r in the insertion axis direction J.

As shown in FIGS. 10 to 12, a fixing hole 55n is formed in the connecting tube fixing portion 55q.

The pressing member 55 is placed in the connecting tube 50 by being passed through the second opening portion 50k. When an arc-shaped outer circumferential face of the connecting tube fixing portion 55q abuts against an inner circumferential face of the connecting tube 50 as shown in FIG. 2, if a fixing member 63 is fixed in the fixing hole 55n by being passed through the insertion hole 50n from outside of the connecting tube 50 at a position where an insertion hole 50n formed in the connecting tube 50 and the fixing hole 55n are superimposed on each other as shown in FIG. 3, the pressing member 55 is fixed to the connecting tube 50 in a fixing area J1.

Note that in the fixing area J1, the pressing member 55 is fixed to the connecting tube 50 only at one point by means of the fixing member 63.

This is because if plural fixing points with respect to the connecting tube 50 are provided on the pressing member 55, plural fixing members become prone to interference with the aforementioned various incorporated components passed through the connecting tube 50 and adversely affect each of the incorporated components, and thus it is inevitable to provide a minimum number of fixing point—one fixing point—on the pressing member 55 with respect to the connecting tube 50 by avoiding the second opening portion 50k and notch 50s.

Also, examples of the fixing member 63 include a screw. Thus, examples of the fixing hole 55n include a screw hole. Furthermore, the fixing member 63 allows the pressing member 55 to be detachably connected to the connecting tube 50.

Also, as shown in FIGS. 10 to 12, in that end portion of the pressing member 55 in the direction Q which is opposite the end portion from which the block unit fixing portion 55w stands up, a rotation restriction portion 55d is formed, extending outward in the direction Q. Note that the rotation restriction portion 55d is, for example, tabular in shape.

As shown in FIG. 8, the rotation restriction portion 55d, which is a member fitted in the notch 50s formed in the connecting tube 50, has a length A along the insertion axis direction J.

Being fitted in the notch 50s, the rotation restriction portion 55d is a member configured to prevent the branch channel connection unit 56 provided with the pressing member 55 fixed to the connecting tube 50 by the fixing member 63 only at one point in the fixing area J1 from being rotated in a direction R2 together with the balloon pipe sleeve 52, for example, when the insertion portion 2 is twisted with respect to the operation portion 3 or the balloon channel side grip 3b is rotated, causing the balloon pipe sleeve 52 to tilt especially in the direction R2. Note that the rotation restriction portion 55d is removably inserted into the notch 50s.

In the connecting tube 50, the block unit 57 is placed on the block unit mounting portion 55p.

The block unit 57 is placed on the block unit mounting portion 55p with a proximal end of the block unit 57 in the insertion axis direction J being positioned by abutting against the stepped portion 55rd provided at a distal end of the block unit positioning portion 55r in the insertion axis direction J.

As shown in FIG. 2, a flow path 57r is formed in the block unit 57, extending from a distal end to a proximal end in the insertion axis direction J. As shown in FIG. 13, an opening 57i of the flow path 57r is formed at the distal end of the block unit 57 in the insertion axis direction J.

As shown in FIGS. 2 and 5 to 7, in the connecting tube 50, the opening 57i is connected with the first opening portion 51t of the balloon water injection channel 51 via a connecting member 54.

Specifically, an area of the balloon water injection channel 51 on the side of the first opening portion 51t is connected via the connecting member 54 by intruding into the flow path 57r via the opening 57i. Note that the connecting member 54 allows the first opening portion 51t to be detachably connected to the opening 57i.

Also, as shown in FIG. 13, an inclined surface 57c is formed at the proximal end of the block unit 57 in the insertion axis direction J. Also, the inclined surface 57c is connected with the first end portion 52i of the balloon pipe sleeve 52 and is provided with a connection pipe sleeve 57e having an opening 57t of the flow path 57r. Note that the inclined surface 57c and connection pipe sleeve 57e are exposed outside the connecting tube 50 by passing through the second opening portion 50k.

Regarding connection of the first end portion 52i to the connection pipe sleeve 57e, the first end portion 52i is configured to be restrained to the connection pipe sleeve 57e only by being rotated for example, after being fitted over the connection pipe sleeve 57e.

After the restraining, a non-illustrated rotation stopper prevents rotation of the first end portion 52i relative to the connection pipe sleeve 57e and thus the connection made by the restraining is not broken. Note that the restraining configuration of the first end portion 52i with respect to the connection pipe sleeve 57e is not limited to this configuration.

In this way, as the first end portion 52i of the balloon pipe sleeve 52 is restrained to the connection pipe sleeve 57e, the block unit 57, holds the first end portion 52i in a holding area J2. Note that the holding area J2 is situated forward of the fixing area J1 by being spaced away from the fixing area J1 in the insertion axis direction J.

Also, that face 57h of the block unit 57 which is opposed to the block unit fixing portion 55w in the direction Q abuts against the block unit fixing portion 55w passed through an insertion hole 55m formed in the block unit fixing portion 55w as shown in FIG. 12, fixed by a fixing member 64 as shown in FIGS. 4, 6, and 11, and thereby fixed to the pressing member 55. Note that examples of the fixing member 64 include a screw.

Consequently, the block unit 57 is fixed to the pressing member 55 by the fixing member 64 by being placed on the block unit mounting portion 55p.

Note that the fixing member 64 allows the block unit 57 to be detachably connected to the pressing member 55. Also, the block unit 57 may be formed integrally with the pressing member 55.

Furthermore, as shown in FIGS. 6 and 7, a face 57f of the block unit 57 opposed to the face 57h in the direction Q abuts an edge portion 50kf of the second opening portion 50k shown in FIG. 9 and thereby prevents the branch channel connection unit 56 provided with the pressing member 55 fixed to the connecting tube 50 by the fixing member 63 only at one point in the fixing area J1 from being rotated in a direction R1 together with the balloon pipe sleeve 52, for example, when the insertion portion 2 is twisted with respect to the operation portion 3 or the balloon channel side grip 3b is rotated, causing the balloon pipe sleeve 52 to tilt in the direction R1.

That is, even if the rotation restriction portion 55d is not fitted in the notch 50s, the abutment of the face 57f against the edge portion 50kf prevents the branch channel connection unit 56 from being rotated in the direction R1 together with the balloon pipe sleeve 52.

Note that by being fitted in the notch 50s, the rotation restriction portion 55d also prevents the branch channel connection unit 56 from being rotated in the direction R1 together with the balloon pipe sleeve 52 when the balloon pipe sleeve 52 is tilted in the direction R1.

Thus, according to the present embodiment, since the rotation restriction portion 55d is fitted in the notch 50s and the face 57f of the block unit abuts the edge portion 50kf, even if the balloon pipe sleeve 52 is tilted in a rotation direction R, the balloon pipe sleeve 52 and the branch channel connection unit 56 are prevented from being rotated.

This reduces a tilting force applied to the fixing area J1 in which the pressing member 55 is fixed to the connecting tube 50 only at one point by means of the fixing member 63, i.e., a tilting force applied to the branch channel connection unit 56 even when the balloon pipe sleeve 52 is tilted in the rotation direction R. Thus, tilting forces applied to a connecting area of the first end portion 52i with respect to the connection pipe sleeve 57e and a connecting area of the first opening portion 51t with respect to the opening 57i are reduced, thereby providing a configuration which sufficiently ensures water tightness of each of the connecting areas.

Now, as shown in FIGS. 7, 8, and 10 to 12, a length A of the rotation restriction portion 55d in the insertion axis direction J is set to a length from the holding area J2 of the first end portion 52i of the balloon pipe sleeve 52 in the connection pipe sleeve 57e to the fixing area J1 of the pressing member 55 with respect to the connecting tube 50 by means of the fixing member 63.

This is because since the pressing member 55 is fixed to the connecting tube 50 by the fixing member 63 at one point in the fixing area J1 rearward of the second opening portion 50k in the insertion axis direction J as described above, when the rotation restriction portion 55d is fitted in the notch 50s from the holding area J2 to the fixing area J1 in the insertion axis direction J, the tilting force in the rotation direction R can be received by a fitting area of the rotation restriction portion 55d in the notch 50s over the entire length A.

That is, suppose the rotation restriction portion 55d is shorter than the length A and fitted in a notch 50s with a similar notch width, only around the holding area J2, if a tilting force is applied to the balloon pipe sleeve 52 in the rotation direction R, although rotation of the branch channel connection unit 56 can be prevented, the tilting force is concentrated on the holding area J2, making it difficult to keep the holding area J2 watertight.

However, if the rotation restriction portion 55d has a length A from the holding area J2 to the fixing area J1 in the insertion axis direction J as with the present embodiment, a turning force can be received over the length A from the holding area J2 to the fixing area J1, in other words, the turning force can be scattered over the length A, and thus the tilting force applied to the fixing area J1 and holding area J2 can be reduced.

Thus, in the present embodiment, it has been shown that the rotation restriction portion 55d formed on the pressing member 55 of the branch channel connection unit 56 used for connection between the first end portion 52i of the balloon pipe sleeve 52 and the first opening portion 51t of the balloon water injection channel 51 is fitted in the notch 50s formed in the connecting tube 50.

Also, it has been shown that the pressing member 55 is fixed to the connecting tube 50 by the fixing member 63 at a one point in the fixing area J1 rearward of the holding area J2 in the insertion axis direction J.

Consequently, even if a tilting force is applied to the balloon pipe sleeve 52 in the rotation direction R, the balloon pipe sleeve 52 and branch channel connection unit 56 can be prevented from rotating using a simple configuration which will not adversely affect the aforementioned incorporated components of the connecting tube 50.

This makes it possible to reduce the tilting force in the rotation direction R applied even to a connecting portion between the first opening portion 51*t* of the balloon water injection channel 51 and the first end portion 52*i* of the balloon pipe sleeve 52, i.e., a connecting portion between the connection pipe sleeve 57*e* of the block unit 57 and the first end portion 52*i* of the balloon pipe sleeve 52 and a connecting portion between the opening 57*i* of the block unit 57 and the first opening portion 51*t*.

As described above, in a configuration in which the pressing member 55 is fixed to the connecting tube 50 by the fixing member 63 at one point in the fixing area J1, since the branch channel connection unit 56 is not fixed near the holding area J2 of the first end portion 52*i* with respect to the connection pipe sleeve 57*e*, the tilting force in the rotation direction R tends to be applied to the fixing area J1 in a concentrated manner when the balloon pipe sleeve 52 is tilted in the rotation direction R. However, as described above, when interference with the incorporated components of the connecting tube 50 is taken into consideration, a fixing member configured to fix the pressing member 55 directly to the connecting tube 50 cannot be provided near the holding area J2. Thus, instead of a fixing member, the present embodiment uses a configuration in which the rotation restriction portion 55*d* is fitted in the notch 50*s*.

Consequently, even if a tilting force is applied to the balloon pipe sleeve 52 in the rotation direction R, a simple configuration in which merely the rotation restriction portion 55*d* is fitted in the notch 50*s* can sufficiently ensure water tightness of the connecting portion between the connection pipe sleeve 57*e* of the block unit 57 and the first end portion 52*i* of the balloon pipe sleeve 52 as well as the connecting portion between the opening 57*i* of the block unit 57 and the first opening portion 51*t*.

Also, it has been shown that in the insertion axis direction J, the rotation restriction portion 55*d* is fitted in the notch 50*s* over a fitting length corresponding to the length A from the fixing area J1 to the holding area J2 described above.

Consequently, the tilting force applied to the balloon pipe sleeve 52 and branch channel connection unit 56 in the rotation direction R can be scattered over the length A, making it possible to sufficiently ensure water tightness of the connecting portion with the first end portion 52*i* of the balloon pipe sleeve 52 as well as the connecting portion between the opening 57*i* of the block unit 57 and the first opening portion 51*t*.

Also, since the pressing member 55 can be assembled easily onto the connecting tube 50 simply by fitting the rotation restriction portion 55*d* in the notch 50*s* without using fixing members such as screws other than the fixing member 63, ease of assembly can be improved.

Thus, the present invention provides the endoscope 1 which can restrict the rotation of the balloon pipe sleeve 52 and uses a simple configuration to reduce the tilting force applied to the fixing section between the balloon pipe sleeve 52 and balloon water injection channel 51 when a tilting force is applied to the balloon pipe sleeve 52.

Now an exemplary configuration of the ultrasound endoscope 1 used in the present embodiment will be described below with reference to FIG. 14. FIG. 14 is a diagram showing an ultrasound endoscope apparatus equipped with the ultrasound endoscope of FIG. 1.

As shown in FIG. 14, the ultrasound endoscope apparatus 100 includes the ultrasound endoscope 1, a light source apparatus 11, a video processor 12, an ultrasound observation apparatus 14, a suction pump 15, a water feeding tank 16, and a syringe 200.

Principal part of the ultrasound endoscope 1 is made up of an elongated insertion portion 2, an operation portion 3, a flexible universal cord 4 extending from the operation portion 3, and an endoscope connector 5 provided on an extending end of the universal cord 4.

The endoscope connector 5 is provided with a light source connector 6, an electrical connector 7, an ultrasound connector 8, a suction pipe sleeve 9, and an air/water feeding pipe sleeve 10.

The light source connector 6 is configured to be detachably connected with the light source apparatus 11 configured to supply illuminating light into a subject via the light guide described above.

Also, the electrical connector 7 is configured to be detachably connected with the video processor 12 configured to perform various signal processing and the like via the above-mentioned image guide and signal cable.

Furthermore, the ultrasound connector 8 electrically connected with a connector 45 provided on a proximal end side of the ultrasound transducer cable 40 extending out from the ultrasound transducer in the ultrasound transducer unit 30 is configured to be detachably connected with the ultrasound observation apparatus 14 via an ultrasound cable 13.

Also, the suction pipe sleeve 9 provided in an opening in another end of the treatment instrument insertion channel 29 is configured to be detachably connected with the suction pump 15 via a non-illustrated suction tube. Furthermore, the air/water feeding pipe sleeve 10 connected to the above-mentioned fluid supply conduit is configured to be detachably connected with the water feeding tank 16 via a non-illustrated air/water feeding tube.

The ultrasound observation apparatus 14 is designed to perform various operation control over the ultrasound endoscope 1, including, for example, drive control of the ultrasound transducer, perform signal processing on electrical signals acquired through the drive control of the ultrasound transducer, and thereby generate a video signal.

Note that the video signal generated by the ultrasound observation apparatus 14 is outputted to a non-illustrated display apparatus. As a result, an ultrasound image is displayed on a screen of the display apparatus which has received the video signal.

Starting from the distal end side, the insertion portion 2 of the ultrasound endoscope 1 includes a distal end portion 21, a bending portion 22 configured to be bendable, for example, in an up-and-down direction and a left-and-right direction, and a flexible tubular portion 23 having a long length and flexibility, all of which are installed consecutively.

Note that the ultrasound transducer unit 30 and balloon 90 described above are located on a distal end side of the distal end portion 21 and fixed to the distal end portion 21.

The operation portion 3 is provided with bending operation knobs 25 and 26 used to perform a bending operation of the bending portion 22. Also, at a position on the side of insertion portion 2, the operation portion 3 is provided with the treatment instrument insertion pipe sleeve 27 used to introduce a treatment instrument into the body through the treatment instrument insertion channel 29. Furthermore, at a position on the side of insertion portion 2, the operation portion 3 is provided with the balloon pipe sleeve 52 used to supply the ultrasound transmission medium to the balloon 90 through the balloon water injection channel 51, where the balloon pipe sleeve 52 is connectable with the syringe 200.

The video processor 12 is designed to perform signal processing on an electrical signal transmitted from a non-illustrated image pickup unit provided in the distal end portion 21, thereby generate a standard video signal, output the video signal to a non-illustrated display apparatus, and display an endoscopic observation image on the screen of the display apparatus.

Note that the configuration of the ultrasound endoscope 1 described above is strictly exemplary and, of course, is not limited to the configuration of FIG. 14.

Also, although in the present embodiment described above, the endoscope 1 has been described by citing an ultrasound endoscope as an example, of course, the present invention is also applicable to endoscopes other than ultrasound endoscopes.

Furthermore, although the balloon water injection channel 51 configured to supply the ultrasound transmission medium to the balloon 90 has been cited as an example of the tubular main channel and the balloon pipe sleeve 52 connected with the syringe 200 configured to inject the ultrasound transmission medium has been cited as an example of the tubular branch channel, this is not restrictive and, needless to say, other conduits may be used as well.

Regarding the other conduits, for example, the treatment instrument insertion channel 29 may be the main channel and the treatment instrument insertion pipe sleeve 27 may be a branch channel. In that case, a midsection of the treatment instrument insertion channel opens as a first opening portion in the balloon channel side grip 3b and the first opening portion is connected with a first end portion of the treatment instrument insertion pipe sleeve 27 via the branch channel connection unit 56.

What is claimed is:

1. An endoscope comprising:
   an insertion portion to be inserted into a subject;
   an operation portion connected to a proximal end side of the insertion portion;
   a main channel configured to be tubular and placed in the insertion portion and the operation portion;
   a first opening portion located at the operation portion and formed at a proximal end of the main channel;
   a branch channel provided with a first end portion and a second end portion, where the second end portion opens outside the operation portion;
   a branch channel connection unit connected so as to be communicated with the first opening portion of the main channel and the first end portion of the branch channel;
   a rotation restriction portion provided on the branch channel connection unit;
   a connecting tube which is fixed to the operation portion, and on which the branch channel connection unit is assembled; and
   a notch which is formed through the connecting tube between an inside and an outside of the connecting tube, and to which the rotation restriction portion is fitted such that the rotation restriction portion protrudes out of the connecting tube;
   wherein the main channel is a balloon water injection channel for supplying an ultrasound transmission medium to a balloon which is provided at the insertion portion, the balloon water injection channel being provided separately from a treatment instrument insertion channel arranged inside the insertion portion; and
   the endoscope further comprises an ultrasound transducer provided at a distal end side of the insertion portion, the ultrasound transducer being configured to transmit and receive ultrasound.

2. The endoscope according to claim 1, wherein the branch channel connection unit comprises:
   a pressing member fixed to the connecting tube by a fixing member and provided with the rotation restriction portion, the fixing member fixing the branch channel connection unit to the connecting tube; and
   a block unit fixed to the pressing member and configured to restrain the first end portion of the branch channel.

3. The endoscope according to claim 1, wherein:
   a fixing area in which the branch channel connection unit is fixed to the connecting tube by a fixing member is spaced away from a holding area of the first end portion of the branch channel on the branch channel connection unit toward a proximal end, the fixing member fixing the branch channel connection unit to the connecting tube; and
   the rotation restriction portion fitted in the notch formed through the connecting tube extends from the holding area to the fixing area of the insertion portion in an insertion axis direction.

4. The endoscope according to claim 1, wherein the connecting tube comprises a second opening portion used to introduce the branch channel connection unit into the connecting tube.

* * * * *